US008838209B2

(12) United States Patent
Mestha et al.

(10) Patent No.: US 8,838,209 B2
(45) Date of Patent: Sep. 16, 2014

(54) DERIVING ARTERIAL PULSE TRANSIT TIME FROM A SOURCE VIDEO IMAGE

(75) Inventors: Lalit Keshav Mestha, Fairport, NY (US); Survi Kyal, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 270 days.

(21) Appl. No.: 13/401,286

(22) Filed: Feb. 21, 2012

(65) Prior Publication Data

US 2013/0218028 A1 Aug. 22, 2013

(51) Int. Cl.
*A61B 5/00* (2006.01)

(52) U.S. Cl.
USPC ............................ 600/473; 600/407; 600/476

(58) Field of Classification Search
USPC .......................................... 600/407, 473–478
See application file for complete search history.

(56) References Cited

U.S. PATENT DOCUMENTS 5,630,422 A * 5/1997 Zanakis ........................ 600/473

FOREIGN PATENT DOCUMENTS

WO W02012007423 A1 1/2012

OTHER PUBLICATIONS

European Search Report, dated Jun. 12, 2013, for EP 13 15 5181.
Allen, John, “Photoplethysmography and its application in clinical physiological measurement”, Physiological Measurement, vol. 28, No. 3, Mar. 1, 2007, pp. R1-R39.
Kalsi, Mastan Singh, “Design of Arterial Blood Pressure, Heart Rate Variability, and Breathing Rate Monitoring Device”, Electrical and Biomedical Engineering Design Project, Apr. 23, 2009, pp. 1-65.
Norris, Suzette, “Innovation Conversation: What Some Xerox Researches Do on their Lunch Hour”, Xerox Newsroom News & Features, Feb. 8, 2013.
Mestha, et al., “Estimating Cardiac Pulse Recovery From Multi-Channel Source Data Via Constrained Source Separation”, U.S. Appl. No. 13/247,683, filed Sep. 28, 2011.
Mestha et al., “Filtering Source Video Data Via Independent Component Selection”, U.S. Appl. No. 13/281,975, filed Nov. 8, 2011.
Mestha et al., “Method for Classifying a Pixel of a Hyperspectral Image in a Remote Sensing Application”, U.S. Appl. No. 13/023,310, filed Mar. 3, 2011.
Wang et al., “Determining a Total Number Of People in an IR Image Obtained Via an IR Imaging System”, U.S. Appl. No. 12/967,775, filed Jan. 4, 2011.
Wang et al., “Determining a Number Of Objects in an IR Image”, U.S. Appl. No. 13/086,006, filed Apr. 28, 2011.

(Continued)

*Primary Examiner* — Peter Luong
(74) *Attorney, Agent, or Firm* — Philip E. Blair; Fleit Gibbons Gutman Bongini & Bianco P.L.

(57) ABSTRACT

What is disclosed is a system and method for determining an arterial pulse transit time of a subject of interest in a remote sensing environment. A video imaging system is used to capture a time varying source images of a proximal and distal region of a subject intended to be analyzed for arterial pulse transit time. A time series signal for each of the proximal and distal regions is extracted from the source images and a phase of each of the extracted time series signals is computed. A difference is then computed between these phases. This phase difference is a monotonic function of frequencies in the signals. From the monotonic function, an arterial pulse transit time of the subject is extracted. The subject's arterial pulse transit time is then communicated to a computer system. The computer system determines blood pressure, blood vessel blockage, blood flow velocity, or a peripheral neuropathy.

25 Claims, 4 Drawing Sheets

START — 200
RECEIVE A TIME VARYING SOURCE VIDEO IMAGE OF A SUBJECT OF INTEREST — 202
PROCESS THE VIDEO IMAGES TO IDENTIFY A PROXIMAL AND DISTAL REGION OF THE SUBJECT WHICH CONTAIN EXPOSED SKIN — 204
EXTRACT VIDEO IMAGES ASSOCIATED WITH EACH OF THE PROXIMAL AND DISTAL REGIONS TO OBTAIN A TIME SERIES SIGNAL FOR EACH CHANNEL — 206
COMPUTE A PHASE ANGLE WITH RESPECT TO FREQUENCY FOR EACH OF THE TIME SERIES SIGNALS TO OBTAIN A PHASE DIFFERENCE CURVE OF FREQUENCIES IN THESE SIGNALS — 208
COMPUTE A FIRST DERIVATIVE OF THE PHASE DIFFERENCE CURVE TO OBTAIN A PULSE TRANSIT TIME BETWEEN THE PROXIMAL AND DISTAL REGIONS — 210
COMMUNICATE THE ARTERIAL PULSE TRANSIT TIME TO A COMPUTER DEVICE — 212
STOP

(56) References Cited

OTHER PUBLICATIONS

Wang, et al., "Post-Processing a Multi-Spectral Image for Enhanced Object Identification", U.S. Appl. No. 13/324,368, filed Dec. 28, 2011.
Mestha et al., "Removing Environment Factors From Video Signals Captured for Biomedical Measurements", U.S. Appl. No. 13/401,207, filed Feb. 21, 2012.
G.L. Pressman and P.M. Newgard, "A Transducer for the Continuous External Measurement of Arterial Blood Pressure", External Measurement of Blood Pressure, IEEE Transactions on Bio-Medical Electronics, Apr. 1963, pp. 73-81.
Kalju Meigas, et al., "Continuous Blood Pressure Monitoring Using Pulse Wave Delay", Proposed Paper; Engineering in Medicine and Biology Society, 2001, vol. 4, pp. 3171-3174, Proceedings of the 23rd Annual Int'l Conf. of the IEEE.
J. Penaz, "Photoelectric Measurement of Blood Pressure, Volume and Flow in the Finger", Dresden, 10th Int. Conf. Med. and Biol. Engineering, 1973, Session 7, N2, Haemodynamics I, pp. 161-164.
Xl Aubert, J. Muehlsteff, "A Model-Based Study of the Influence of Vaso-Active Drugs on Pulse Delays Measured from the Electrocardiogram", Computers in Cardiology 2007:34:383-386.
Jochanan E. Naschitz et al., "Pulse Transit Time by R-Wave-Gated Infrared Photoplethysmography: Review of the Literature and Personal Experience", Journal of Clinical Monitoring and Computing (2004) 18: 333-342, Springer 2005.
Andrew Reisner et al., "Utility of the Photoplethysmogram in Circulatory Monitoring", Anesthesiology, vol. 108, No. 5, May 2008, pp. 950-958.

* cited by examiner

DERIVING ARTERIAL PULSE TRANSIT TIME FROM A SOURCE VIDEO IMAGE

TECHNICAL FIELD

The present invention is directed to systems and methods for determining the patient's arterial pulse transit time from a source video signal acquired of that patient.

BACKGROUND

The ability to capture physiological signals by non-contact means is highly desirable in the healthcare industry. One physiological signal of importance is the pulse transit time for many reasons, one of which is that the pulse transit time has a correlation with blood pressure. To obtain such measurements, electrodes of an electro-cardiogram (ECG) device need to be attached directly to the patient's skin. This can be a problem in neonatal intensive care units caring for premature babies with sensitive skin.

Accordingly, what is needed in this art are systems and methods which can obtain a patient's arterial pulse transit time in a non-contact, non-invasive manner.

INCORPORATED REFERENCES

The following U.S. Patents, U.S. Patent Applications, and Publications are incorporated herein in their entirety by reference.

"Estimating Cardiac Pulse Recovery From Multi-Channel Source Data Via Constrained Source Separation", U.S. patent application Ser. No. 13/247,683, by Mestha et al.

"Filtering Source Video Data Via Independent Component Selection", U.S. patent application Ser. No. 13/281,975, by Mestha et al.

"Method For Classifying A Pixel Of A Hyperspectral Image In A Remote Sensing Application", U.S. patent application Ser. No. 13/023,310, by Mestha et al.

"Determining A Total Number Of People In An IR Image Obtained Via An IR Imaging System", U.S. patent application Ser. No. 12/967,775, by Wang et al, which discloses a ratio method for classifying pixels in an IR image.

"Determining A Number Of Objects In An IR Image", U.S. patent application Ser. No. 13/086,006, by Wang et al, which discloses a correlation method and a best fitting reflectance method for classifying pixels in an IR image.

"Post-Processing A Multi-Spectral Image For Enhanced Object Identification", U.S. patent application Ser. No. 13/324,368, by Wang et al.

"Removing Environment Factors From Signals Generated From Video Images Captured For Biomedical Measurements", U.S. patent application Ser. No. 13/401,207, by Mestha et al.

BRIEF SUMMARY

What is disclosed is a system and method for determining a subject of interest's arterial pulse transit time from time varying source signals generated from video images. In one embodiment, a video imaging system is used to capture a time varying source signal of a proximal and distal region of a subject of interest. The image frames are processed to isolate localized areas of a proximal and distal region of exposed skin of the subject. A time series signal for each of the proximal and distal regions is extracted from the source video images and a phase of each of the extracted signals is computed for each region. A phase difference is computed between the time series signals of the two regions to obtain a monotonic function of frequencies in those signals. From the monotonic function, the subject's arterial pulse transit time is derived. The subject's arterial pulse transit time is then communicated to a computer system. In various embodiments hereof, the computer system proceeds to further determine the subject's blood pressure, a blood vessel dilation over time, a blood vessel blockage, a blood flow velocity, or the existence of a peripheral neuropathy in the subject.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for determining an arterial pulse transit time between a proximal and distal region of a subject of interest from source video images acquired of that subject using a video imaging system.

NON-LIMITING DEFINITIONS

A "subject of interest", as used herein, refers to any subject which is capable of registering an arterial pulse. The present method applies equally to any subjects capable of registering an arterial pulse. Use of the terms herein for explanatory purpose, such as "person" or "patient", are not to be viewed as limiting the scope of the appended claims to human subjects.

"Proximal" (from the Latin proximus: meaning nearest to) refers to a point that is nearer to the source of the arterial pulse which is in the ascending aorta. Note that the systemic arterial system originate from the aorta. As left ventricle of the heart contracts blood exits from the ascending aorta in the form of waves and flows into systemic arteries. The heart is located near the anterior chest wall, directly posterior to the sternum. For arterial pulse measurement purposes, a proximal point in an artery is a point which is closer to the heart, i.e., upstream from the distal point.

"Distal" (from the Latin distare: meaning away from) refers to a point that is farther from a center of the body. For arterial pulse measurement purposes, the distal point in the artery is a point which is farther from the heart, i.e., upstream or downstream from the proximal point as the arterial network carries blood upstream & downstream through the branches of the aortic arch and the descending aorta. By drawing an imaginary line between the proximal and distal points, a proximo-distal axis is created. The elbow is proximal to the wrist but distal to the shoulder since the blood flows from brachial arteries towards the wrist through radial and ulnar arteries. Blood vessels may also be labeled as "ostial" (referring to point where the blood vessel branches off) and "distal" (referring to a point away from the branch point).

An "arterial pulse wave" is a pressure wave created throughout the vascular system when the left ventricle of the heart muscle contracts and pushes a volume of blood into the aorta. This generates a perturbation that travels from the heart and down into the arterial network. An arterial pulse wave has two primary components, i.e., a forward traveling wave when the left ventricle contracts, and a reflected wave returning back from the peripheral. The actual pressure in the aorta is the sum of the initial wave and the reflected wave.

Figure 1:
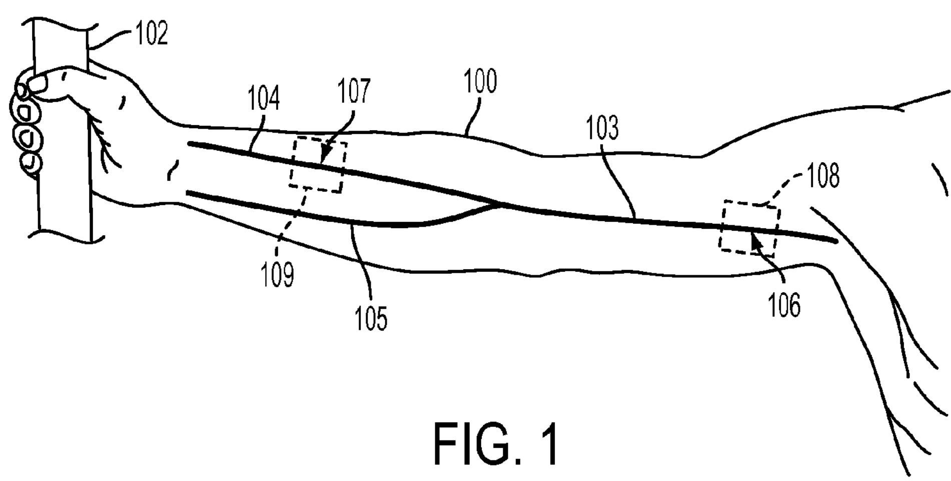
FIG. 1 shows a subject of interest's right arm extremity clutching a pole to illustrate two proximal and distal points in the arterial system of the human arm.

The "pulse transit time" refers to the time it takes a pressure pulse to travel from a proximal arterial site to a distal arterial site. Pulse transit time (PTT) is a function of the pulse wave velocity which, in turn, is a function of the blood pressure, vessel diameter, blood density. Localized PTT is used as an indirect marker of various pathologic conditions. PTT has high correlations when utilized as a surrogate monitor of BP changes. Present literature suggests that description of disease-specific cardiovascular reactivity pattern is feasible with techniques that are based upon PTT. PTT signals can be calibrated to extract beat-to-beat blood pressure and blood velocity in the patient's vascular network including facilitating for variety of diagnosis such as, for example, blood vessel dilation over time, vessel blockage between two points (or regions) of interest, peripheral neuropathy for diabetic patients etc. FIG. 1 shows a subject of interest's right arm 100 extended outward and clutching a section of a pole 102. The subject's brachial artery 103 extends down the arm and branches into the radial and ulnar arteries, at 104 and 105 respectively. A point 106 in the brachial artery is proximal to a point 107 in the radial artery. In the illustrated example of FIG. 1 and for discussion purposes, the pulse transit time is the time it takes for the arterial pulse wave to travel from point 106 in proximal region 108 to point 107 within distal region 109. Moreover, if the forearm of the subject is moving while the video is being acquired then the respective regions have to be identified in each video frame for processing. This can be done by performing identification of arterial pathway via special image processing techniques and then tracking arterial pathway on a frame by frame basis.

An "imaging sensor" is a device for capturing source video data over one or more channels. The imaging sensor may be a device with a high frame rate and high spatial resolution such as, for example, a monochrome camera for capturing black/white video images, or a color camera for capturing color video images. The imaging sensor may be a spectral sensor such as a multi-spectral or hyperspectral system. Spectral sensors are devices which have relatively low frame rates and low spatial resolution but high spectral resolution. The imaging sensor may be a hybrid device capable of operating in a conventional video mode with high frame rate and high spatial resolution, and a spectral mode with low frame rates but high spectral resolution. Imaging sensors comprising standard video cameras and those comprising spectral sensors are readily available from many vendors in various streams of commerce.

A "source video images" refers to time varying video images acquired using an imaging sensor. A source video image can be any combination of: NIR images, RGB images, RGB with NIR images, multi-spectral images, and hyperspectral video images. It should be appreciated that when the video capture is made in the NIR band, enough illumination will be required to image in the infrared wavelength.

A "remote sensing environment" refers to non-contact, non-invasive sensing, i.e., the imaging sensor does not physically contact the subject being sensed. The environment may be any settings such as, for example, a hospital, ambulance, medical office, and the like.

Example Flow Diagram of One Embodiment

Figure 2:
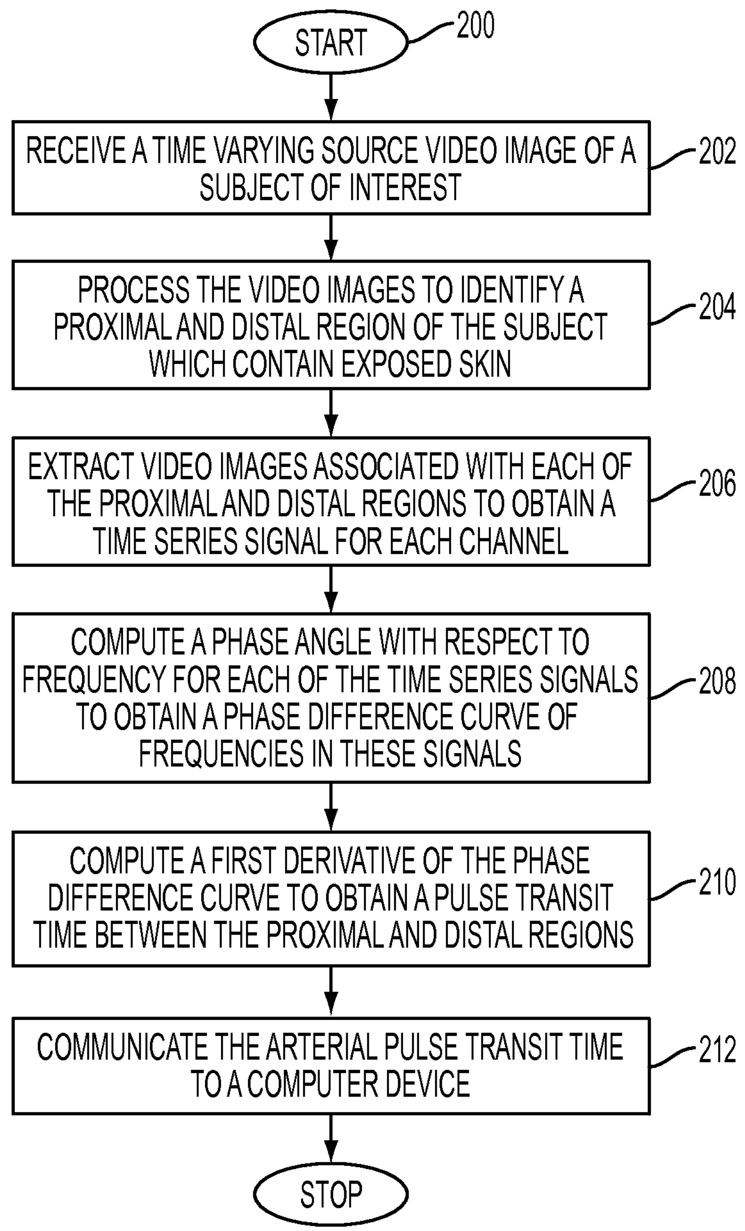
FIG. 2 is a flow diagram which illustrates one embodiment of the present method for determining an arterial pulse transit time between a proximal and distal region of a subject of interest from source video images acquired using a video imaging system in a non-contact, remote sensing environment.

Reference is now being made to the flow diagram of FIG. 2 which illustrates one embodiment of the present method for determining an arterial pulse transit time between a proximal and distal region of a subject of interest from source video images acquired using a video imaging system in a non-contact, remote sensing environment. Flow processing begins at step 200 and immediately proceeds to step 202.

At step 202, a time varying source images is received which has been captured of a subject of interest. The source video images have been acquired over at least one channel of a video imaging system. The source images comprise a plurality of image frames.

At step 204, the video images are processed to identify a proximal and a distal region of the subject which contain areas of exposed skin. Example proximal and distal regions are shown and described with respect to regions 108 and 109 of FIG. 1, respectively. Areas of exposed skin can be determined in an image by analyzing the video images, on a frame-by-frame basis, and classifying the pixels comprising in those image frames. Pixels classified as human skin can be identified using, for example, the above-incorporated pixel classification methods.

At step 206, video images associated with each of the identified proximal and distal regions are extracted from the source images to obtain a time series signal for each channel. This can be effectuated by computing an average of all pixels in each of the identified proximal and distal regions within each image frame to obtain a channel average per frame for each of the regions. A global channel average can then be computed, for each channel, by adding the channel averages across multiple frames and dividing by the total number of frames. The channel average is subtracted from the global channel average and the result is divided by a global channel standard deviation to obtain a zero-mean unit variance time series signal for each of the proximal and distal regions. These time series signals contain frequency components. For the purpose of determining the pulse transit time, processing with only a single color channel is adequate. For example, in a RGB video, time series signals from the green channel contain a sufficient signal. Once normalized time series signals have been obtained for each of the proximal and distal regions, these are then subjected to a pre-filtering to remove undesirable frequencies using a FFT. The resulting pre-processed and pre-filtered time series signals contain the sum total of volumetric pressure changes within each region. Further pre-processing can be done to extract the source blood volume signals (such as the plethysmographic signals) using blind source separation algorithms such as the independent component analysis or the constrained independent component analysis as described in the aforementioned references. It should be understood that the volume changes in the first and second regions are due to all the blood vessels in each of those regions. Arterial pulsations are a dominant component in these signals. Components from smaller structures such as capillaries and terminal arterioles are less significant as these only provide a minor contribution to the registered pulsations.

If camera related noise or other environmental factors affecting the video capture are present, compensation can be introduced as described in the above-incorporated reference entitled: "Removing Environment Factors From Signals Generated From Video Images Captured For Biomedical Measurements", By Mestha et al. The post-compensated signal contains decorrelated and noise corrected channels, i.e., environmentally compensated signals for each of the proximal and distal regions.

At step 208, a phase angle is computed for each of the time series signals for a selected channel of interest. Only one of the channels will need to be used to determine the phase difference. If a source separation algorithm is used then the source signals from proximal and distal regions will be used to compute the phase difference. One of ordinary skill will readily understand how to compute a phase angle $\phi(\omega)$ with respect to frequency co given a time series signal.

Figure 3:
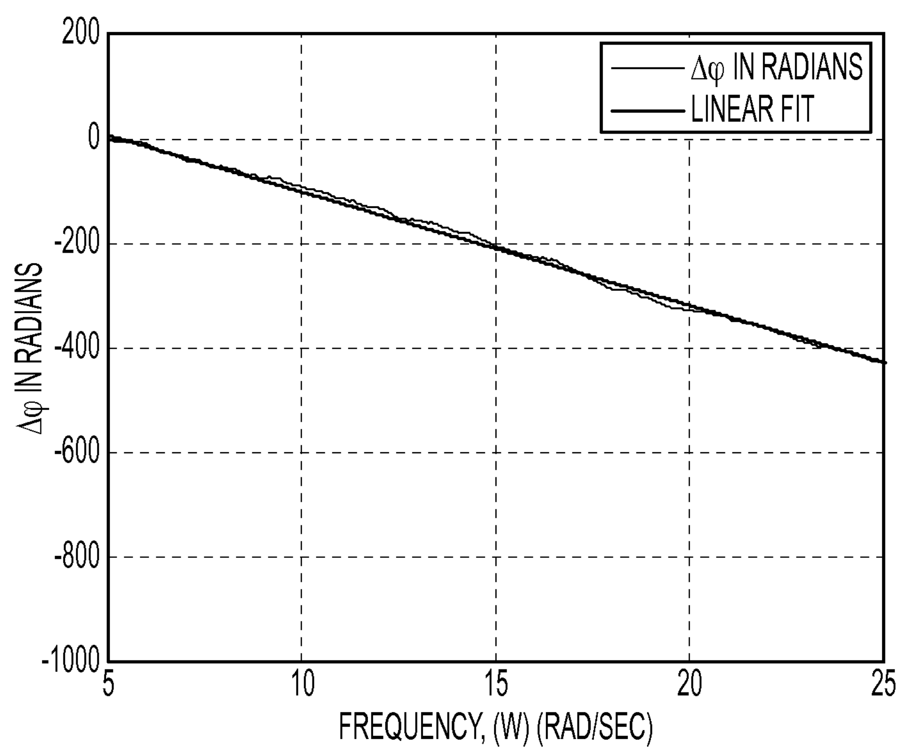
FIG. 3 is a plot of the phase differential with respect to frequency (rad/sec) for one test embodiment in which the pulse transit time was obtained for video images with proximal region selected on the region around the neck and face to a distal region near the back of the palm.

A phase difference is computed between the phases of each of the time series signals. If $\phi_1(\omega)$ is the phase of the time series signal of the proximal region and $\phi_2(\omega)$ is the phase of the time series signal of the distal region then the phase difference $\Delta\phi$ is given by: $\phi_1(\omega)-\phi_2(\omega)$. The phase difference signal is linear with respect to frequency since all frequencies go through similar delay between two regions and that the resulting phase difference curve is a monotonic function of frequencies contained within these signals. FIG. 3 is a plot of the phase differential with respect to frequency (rad/sec). Along the X-axis, 5 rad/sec and 25 rad/sec.

At step 210, compute a first derivative of the phase difference curve (monotonic function) with respect to frequency. The first derivative of the phase difference curve produces a pulse transit time. In FIG. 3, the PTT is the slope of the line=21.7 secs. This PTT was obtained for video images with proximal region selected on the region around the neck and face to distal region near the back of the palm.

At step 212, the subject's arterial pulse transit time is communicated to a computer system. In this embodiment, further processing stops. In other embodiments, the computer system determines, from the arterial pulse transit time, any of: a blood pressure in the subject's vascular network, a blood vessel dilation over time, a blood vessel blockage, a blood flow velocity, and the existence of a peripheral neuropathy in the subject.

It should be appreciated that the flow diagrams hereof are illustrative. One or more of the operative steps illustrated in the flow diagram may be performed in a differing order. Other operations, for example, may be added, modified, enhanced, condensed, integrated, or consolidated. Such variations are intended to fall within the scope of the appended claims. All or portions of the flow diagrams may be implemented partially or fully in hardware in conjunction with machine executable instructions.

Source Signal Processing System

Figure 4:
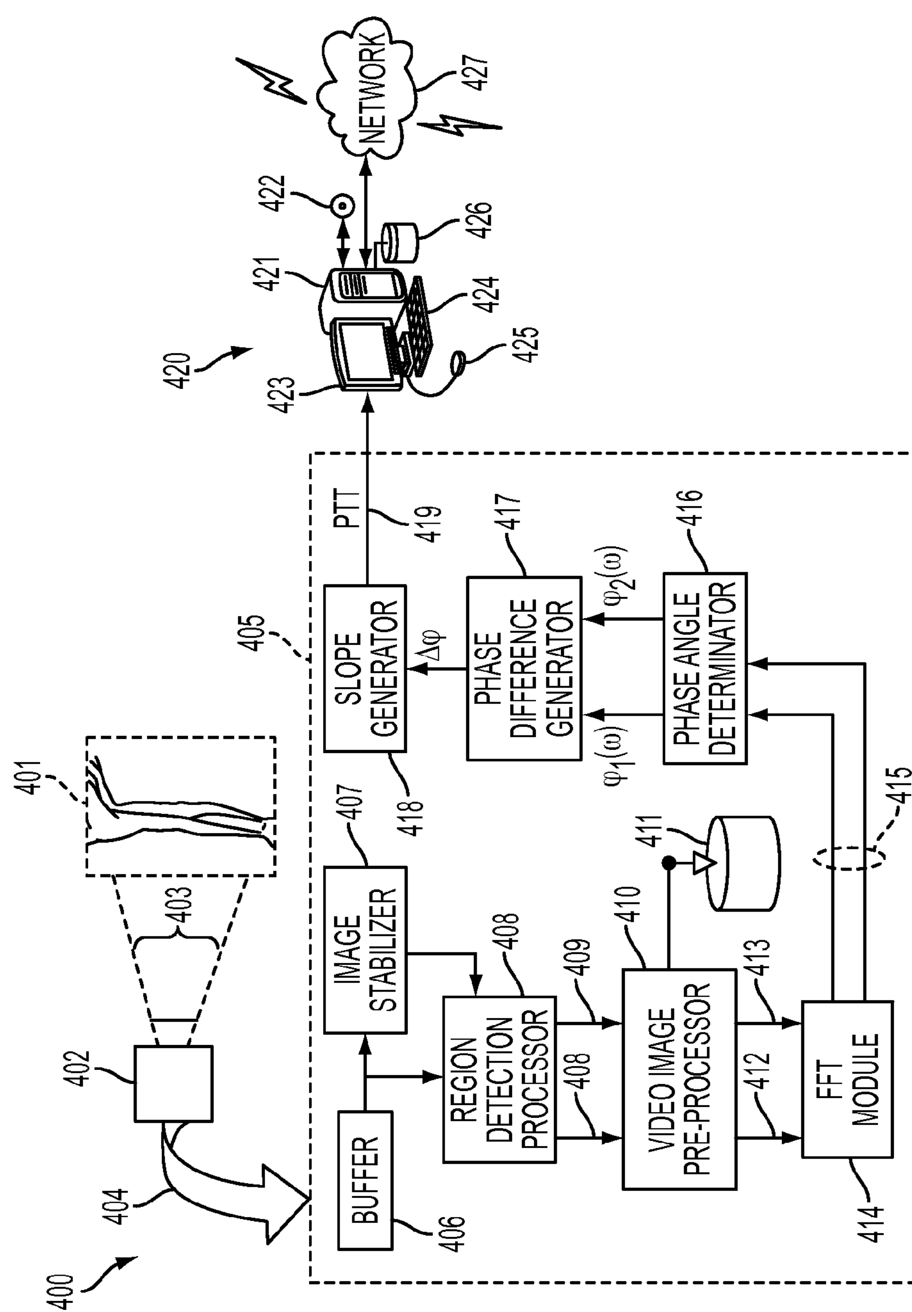
FIG. 4 is a block diagram of an example networked video image processing system wherein various aspects of the present method as described with respect to the flow diagram of FIG. 2 are implemented.

Reference is now being made to FIG. 4 which is a block diagram of an example networked video image processing system 400 wherein various aspects of the present method as described with respect to the flow diagram of FIG. 2 are implemented.

In FIG. 4, imaging sensor 402 acquires source video images 401 of a subject of interest (only shown is the subject's right arm) captured in the video camera's field of view 403. The source video images are acquired over at least one imaging channel and the signals 404 for each channel are communicated to Video Image Processing System 405 wherein various aspects of the present method are performed. System 405 is shown comprising a Buffer 406 for buffering the source signal for processing. Buffer 406 may further store data, formulas, mathematical representations, and the like, as are needed to process the source video images in accordance with the teachings hereof. Image Stabilizer Module 407 processes the images to compensate, where needed, for anomalies such as motion induced blur, imaging blur, slow illuminant variation, and the like. Region Detection Processor 408 receives the video images and processes the images contained therein in order to determine a proximal and a distal region (at 408 and 409, respectively) of the subject in the captured video images 401 which contain regions of exposed skin. One or more frames of the captured source video image may be communicated by pathways not shown to workstation 420 for display 423 thereon such that the user can select any of the proximal and distal regions from any of the captured image frames using, for example, a rubber-band box created by clicking and dragging a mouse or by otherwise highlighting localized areas of exposed skin in one or more image frames of the video sequence such as, for example, proximal and distal regions 108 and 109 of FIG. 1, for processing, (at 408 and 409, respectively). Portions of the source images associated with each of the proximal and distal regions are provided to Video Image Pre-Processor 410 which receives the source images associated with each of the identified proximal and distal regions and extracts a time series signal from the source images for each channel of each region. Various signal components may be stored/retrieved to storage device 411 using communication pathways not shown. The normalized time series signals 412 and 413 extracted for each of the proximal and distal regions, respectively, are provided to FFT Module 414 wherein these time series signals are subjected to a pre-filtering to remove undesirable frequencies. The filtered time series signals, collectively at 415, are provided to Phase Angle Determinator 416 which receives the filtered time series signals for each of the proximal and distal regions and computes a phase $\phi$ with respect to frequency for each of the time series signals for a selected channel of interest, shown as $\phi_1(\omega)$ and $\phi_2(\omega)$, respectively. Phase Difference Generator 417 receives the phases computed for each of the proximal and distal regions for a selected channel of interest, and computes a phase difference $\Delta\phi$. The phase difference, when plotted, comprises a curve such as that shown in the example of FIG. 3. Signal Generator 418 plots the phase difference and computes the slope thereof and outputs the pulse transit time 419. The generated arterial pulse transit time is communicated to networked computer system 420.

Workstation 420 reads/writes to computer readable media 422 such as a floppy disk, optical disk, CD-ROM, DVD, magnetic tape, etc. Case 421 houses a motherboard with a processor and memory, a network card, graphics card, and the like, and other software and hardware. The workstation includes a user interface which, in this embodiment, comprises display 423 such as a CRT, LCD, touch screen, etc., a keyboard 424 and a mouse 425. A user or technician may use the keyboard and/or mouse to identify the proximal and distal regions, set parameters, select images for processing, view results, and the like. It should be appreciated that the workstation has an operating system and other specialized software configured to display a variety of numeric values, text, scroll bars, pull-down menus with user selectable options, and the like, for entering, selecting, or modifying information displayed on display device 423. Various portions of the source video signals captured by video capture device 402 may be communicated to workstation 420 for processing and stored to storage device 426. Workstation 420 is in communication with one or more remote devices of network 427 via a communications interface internal to case 421.

It should be appreciated that some or all of the functionality performed by any of the modules and processing units of the signal processing system 405 can be performed, in whole or in part, by workstation 420. Any of these may be stored to storage device 426 or written to computer media 422. Any of the modules and processing units of FIG. 4 can be placed in communication with storage devices 411 and 426 and may store/retrieve therefrom data, variables, records, parameters, functions, machine readable/executable program instructions required to perform their intended functions. Each of the modules of system 405 may be placed in communication with one or more devices over network 427. Although shown as a desktop computer, it should be appreciated that computer system 420 can be any of a laptop, mainframe, server, or a special purpose computer such as an ASIC, circuit board, dedicated processor, or the like.

Various Embodiments

It should also be appreciated that various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems operating in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through a network. The teachings hereof can be implemented in hardware or software using any known or later developed systems, structures, devices, and/or software by those skilled in the applicable art without undue experimentation from the functional description provided herein with a general knowledge of the relevant arts.

One or more aspects of the methods described herein are intended to be incorporated in an article of manufacture, including one or more computer program products, having computer usable or machine readable media. For purposes hereof, a computer usable or machine readable media is, for example, a floppy disk, a hard-drive, memory, CD-ROM, DVD, tape, cassette, or other digital or analog media, or the like, which is capable of having embodied thereon a computer readable program, one or more logical instructions, or other machine executable codes or commands that implement and facilitate the function, capability, and methodologies described herein. Furthermore, the article of manufacture may be included on at least one storage media readable by a machine architecture or image processing system embodying executable program instructions capable of performing the methodology described in the flow diagrams. The article of manufacture may be included as part of an operating system, a plug-in, or may be shipped, sold, leased, or otherwise provided separately, either alone or as part of an add-on, update, upgrade, or product suite.

It will be appreciated that various of the above-disclosed and other features and functions, or alternatives thereof, may be desirably combined into many other different systems or applications. Various presently unforeseen or unanticipated alternatives, modifications, variations, or improvements therein may become apparent and/or subsequently made by those skilled in the art, which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for determining an arterial pulse transit time between a proximal and distal region of a subject of interest from source video images acquired using a video imaging system in a non-contact, remote sensing environment, the method comprising:

receiving time varying source images acquired over at least one channel of a video imaging system, said source images comprising video images captured of a proximal and distal region of an area of exposed skin of a subject of interest wherein an arterial pulse transit time in that area is desired to be determined;

extracting, from said source images, a time series signal for each of said proximal and distal regions;

computing a phase angle with respect to frequency for each of said time series signals;

determining, using a processor, a phase difference between said computed phases, said phase difference comprising a monotonic function of frequencies in said signals;

extracting, from said monotonic function, an arterial pulse transit time of said subject; and storing said extracted arterial pulse transit time to a storage device.

2. The method of claim 1, wherein said time varying source signal comprises any combination of: NIR images, RGB images, RGB with NIR images, multispectral images, and hyperspectral video images.

3. The method of claim 1, wherein, in advance of extracting said time series signals, further comprising compensating for any of: a motion induced blur, an imaging blur, and slow illuminant variation.

4. The method of claim 1, wherein said video images are acquired by a single NIR channel, further comprising:

partitioning frames from said channel for each region into a non-skin region and a skin region; and performing source separation to obtain both a heart rate signal and a phase difference.

5. The method of claim 1, further comprising converting said signals to a frequency domain via a Fourier transformation.

6. The method of claim 1, wherein said proximal and distal regions comprise, respectively, a first and second localized area of said subject.

7. The method of claim 1, wherein extracting said subject's arterial pulse transit time from said monotonic function comprises determining a slope of said function, said slope being a pulse transition time between said proximal and distal regions.

8. The method of claim 1, further comprising determining, from said arterial pulse transit time, any of: a blood pressure in said subject's vascular network, a blood vessel dilation over time, a blood vessel blockage, a blood flow velocity, and the existence of a peripheral neuropathy.

9. The method of claim 1, further comprising:

processing said video images to determine a region of skin; and isolating said proximal and distal regions from said skin regions.

10. A non-contact video based system for determining an arterial pulse transit time between a proximal and distal region of a subject of interest from source video images acquired using a video camera, the system comprising:

a video imaging system for capturing time varying source images over at least one channel, said source images comprising video images captured of a proximal and distal region of an exposed area of skin of a subject of interest wherein an arterial pulse transit time in that area is desired to be determined; and a processor in communication with said video camera and a memory, said processor executing machine readable instructions for performing:

extracting, from said source images, a time series signal for each of said proximal and distal regions;

computing a phase angle with respect to frequency for each of said time series signals;

determining a phase difference between said phases, said phase difference comprising a monotonic function of frequencies in said signals; and extracting, from said monotonic function, an arterial pulse transit time of said subject.

11. The system of claim 10, wherein said time varying source images comprises any combination of: NIR images, RGB images, RGB with NIR images, multispectral images, and hyperspectral video images.

12. The system of claim 10, wherein, in advance of extracting said time series s, further comprising compensating for any of: a motion induced blur, an imaging blur, and slow illuminant variation.

13. The system of claim 10, wherein said video images are acquired by a single NIR channel, further comprising:

partitioning frames from said channel for each region into a non-skin region and a skin region; and performing source separation to obtain both a heart rate signal and a phase difference.

14. The system of claim 10, further comprising converting said signals to a frequency domain via a Fourier transformation.

15. The system of claim 10, wherein said proximal and distal regions comprise, respectively, a first and second localized area of said subject.

16. The system of claim 10, wherein extracting said subject's arterial pulse transit time from said monotonic function comprises determining a slope of said function, said slope being a pulse transition time between said proximal and distal regions.

17. The system of claim 10, further comprising determining, from said arterial pulse transit time, any of: a blood pressure in said subject's vascular network, a blood vessel dilation over time, a blood vessel blockage, a blood flow velocity, and the existence of a peripheral neuropathy.

18. The system of claim 10, further comprising:

processing said video images to determine a region of skin; and isolating said proximal and distal regions from said skin regions.

19. A computer implemented video-based method for determining an arterial pulse transit time between a proximal and distal region of a subject of interest from source video images acquired using a video imaging system in a non-contact, remote sensing environment, the method comprising:

receiving time varying source images acquired over at least one channel of a video imaging system, said source images comprising video images captured of a proximal and distal region of an area of exposed skin of a subject of interest wherein an arterial pulse transit time in that area is desired to be determined;

processing said video images to determine a region of skin;

isolating said proximal and distal regions from said skin regions;

extracting, from said source images, a time series signal for each of said proximal and distal regions, said proximal and distal regions comprising, respectively, a first and second localized area of said subject;

computing a phase angle with respect to frequency for each of said time series signals;

determining, using a processor, a phase difference between said computed phases, said phase difference comprising a monotonic function of frequencies in said signals;

extracting, from said monotonic function, an arterial pulse transit time of said subject; and storing said extracted arterial pulse transit time to a storage device.

20. The computer implemented method of claim 19, wherein said time varying source images comprises any combination of: NIR images, RGB images, RGB with NIR images, multispectral images, and hyperspectral video images.

21. The computer implemented method of claim 19, wherein said video images are acquired by a single NIR channel, further comprising:

partitioning frames from said channel for each region into a non-skin region and a skin region; and performing source separation to obtain both a heart rate signal and a phase difference.

22. The computer implemented method of claim 19, further comprising converting said signals to a frequency domain via a Fourier transformation.

23. The computer implemented method of claim 19, wherein extracting said subject's arterial pulse transit time from said monotonic function comprises determining a slope of said function, said slope being a pulse transition time between said proximal and distal regions.

24. The computer implemented method of claim 19, further comprising said computer system determining, from said arterial pulse transit time, any of: a blood pressure in said subject's vascular network, a blood vessel dilation over time, a blood vessel blockage, a blood flow velocity, and the existence of a peripheral neuropathy.

25. The computer implemented method of claim 19, further comprising communicating said subject's arterial pulse transit time to a computer system.

* * * * *